(12) United States Patent
Brown et al.

(10) Patent No.: US 10,900,922 B2
(45) Date of Patent: Jan. 26, 2021

(54) POWER REDUCTION IN COMBUSTIBLE GAS SENSORS

(71) Applicant: MSA TECHNOLOGY, LLC, Cranberry Township, PA (US)

(72) Inventors: Michael Alvin Brown, Cranberry Township, PA (US); Meghan E. Swanson, Pittsburgh, PA (US); Mark Flori Zanella, Sr., Chicora, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 227 days.

(21) Appl. No.: 16/037,882

(22) Filed: Jul. 17, 2018

(65) Prior Publication Data

US 2020/0025701 A1 Jan. 23, 2020

(51) Int. Cl.
*G01N 27/16* (2006.01)
*G01N 25/30* (2006.01)

(52) U.S. Cl.
CPC ............ *G01N 27/16* (2013.01); *G01N 25/30* (2013.01)

(58) Field of Classification Search
None
See application file for complete search history.

(56) References Cited

U.S. PATENT DOCUMENTS

| | | |
|---|---|---|
| 3,948,810 A | 4/1976 | Hervert |
| 4,097,353 A | 6/1978 | Kishida |
| 4,280,845 A | 7/1981 | Matsushisa |

(Continued)

FOREIGN PATENT DOCUMENTS

| | | |
|---|---|---|
| EP | 0094863 | 11/1983 |
| EP | 0130785 | 3/1988 |

(Continued)

OTHER PUBLICATIONS

Mosely, P.T., Solid State Gas Sensors, Adams Hilger Press, Bristol, England, 18-31 (1987).

(Continued)

*Primary Examiner* — Matthew D Krcha
(74) *Attorney, Agent, or Firm* — Bartony & Associates LLC

(57) ABSTRACT

A system includes a primary combustible gas sensor and a trigger combustible gas sensor including a first trigger element of low-thermal-mass which includes a first trigger heating element in operative connection with electronic circuitry. The trigger combustible gas sensor also includes a second trigger element of low thermal mass including a second trigger heating element. The second trigger element is also in operative connection with the electronic circuitry. The electronic circuitry further has a first trigger mode of operating in which the first trigger element is heated to a temperature at or above a temperature at which the first trigger element causes combustion of the at least one combustible gas analyte and wherein the second trigger element is operated as a trigger compensating element. The electronic circuitry is configured to operate the trigger combustible gas sensor to detect a value of a response at or above a threshold value. The primary combustible gas sensor is activated from a low-power state upon the threshold value being detected by the trigger combustible gas sensor.

26 Claims, 2 Drawing Sheets

(56) References Cited

U.S. PATENT DOCUMENTS

| | | | |
|---|---|---|---|
| 4,343,768 A * | 8/1982 | Kimura | G01N 27/16 338/34 |
| 4,533,520 A | 8/1985 | Bossart | |
| 4,569,826 A | 2/1986 | Shiratori | |
| 4,627,269 A | 12/1986 | Forster | |
| 4,950,628 A | 8/1990 | Landon | |
| 5,225,786 A * | 7/1993 | Vaughn | G01N 27/16 324/693 |
| 5,234,837 A | 8/1993 | Accorsi | |
| 5,368,713 A | 11/1994 | Friese | |
| 5,401,470 A | 3/1995 | Poli | |
| 5,423,973 A | 6/1995 | Friese | |
| 5,494,701 A | 2/1996 | Clough | |
| 5,528,225 A | 6/1996 | Sakai | |
| 5,599,584 A | 2/1997 | Champney, Jr. | |
| 5,780,715 A | 7/1998 | Imblum | |
| 5,841,021 A | 11/1998 | De Castro | |
| 5,902,556 A | 5/1999 | Van De Vyver | |
| 6,019,946 A | 2/2000 | Castillo | |
| 6,071,476 A | 6/2000 | Young | |
| 6,080,219 A | 6/2000 | Jha | |
| 6,131,438 A | 10/2000 | Zanini-Fisher | |
| 6,344,174 B1 | 2/2002 | Miller | |
| 6,548,024 B1 | 4/2003 | Doncaster | |
| 6,663,834 B1 | 12/2003 | Miller | |
| 6,705,152 B2 | 3/2004 | Routkevitch | |
| 6,756,016 B2 | 6/2004 | Miller | |
| 6,812,708 B2 | 11/2004 | Bristol | |
| 7,559,228 B2 | 7/2009 | Baha | |
| 7,833,482 B2 | 11/2010 | Samari | |
| 8,373,568 B2 | 2/2013 | Moe | |
| 8,826,721 B2 | 9/2014 | Zanella, Sr. | |
| 9,228,967 B2 | 1/2016 | Alepee | |
| 9,625,406 B2 | 4/2017 | Zanella, Sr. | |
| 2002/0146352 A1 | 10/2002 | Wang | |
| 2003/0039299 A1 * | 2/2003 | Horovitz | G01N 27/123 374/141 |
| 2004/0208789 A1 | 10/2004 | Miller | |
| 2005/0217370 A1 | 10/2005 | Takahashi | |
| 2006/0228261 A1 | 10/2006 | Iwamoto | |
| 2008/0034841 A1 | 2/2008 | Bahs | |
| 2008/0156076 A1 * | 7/2008 | Samari | G01N 27/16 73/31.05 |
| 2011/0100090 A1 | 5/2011 | Zanella, Sr. | |
| 2012/0318037 A1 | 12/2012 | Lee | |
| 2014/0208838 A1 * | 7/2014 | Moon | G01N 27/16 73/114.75 |
| 2014/0273263 A1 | 9/2014 | Zanella, Sr. | |
| 2017/0024992 A1 | 1/2017 | Chey | |
| 2018/0128763 A1 | 5/2018 | Swanson | |
| 2018/0335411 A1 | 11/2018 | Zanella, Sr. | |
| 2018/0335412 A1 | 11/2018 | Zanella, Sr. | |

FOREIGN PATENT DOCUMENTS

| | | |
|---|---|---|
| EP | 0311964 | 4/1989 |
| EP | 0313390 | 4/1989 |
| EP | 0364982 A2 | 4/1990 |
| EP | 0703449 | 3/1996 |
| EP | 0500598 B1 | 3/1997 |
| EP | 1505385 A1 | 2/2005 |
| GB | 1550615 A | 8/1979 |
| GB | 2067294 | 7/1981 |
| GB | 2121180 | 12/1983 |
| JP | H08247984 | 9/1996 |
| JP | 2000039413 A | 2/2000 |
| JP | 2008096267 | 4/2008 |
| WO | WO2000043765 A1 | 7/2000 |
| WO | WO2006111727 A1 | 10/2006 |
| WO | WO2011053866 A1 | 5/2011 |
| WO | WO2018085026 | 5/2018 |
| WO | WO2018212965 A1 | 11/2018 |
| WO | WO2018212966 A1 | 11/2018 |
| WO | 2020018526 A1 | 1/2020 |

OTHER PUBLICATIONS

Firth, J.G. et al., The Principles of the Detection of Flammable Atmospheres by Catalytic Devices, Combustion and Flame 21, 303-311 (1973).

Cullis, C.F., Eds., Detection and Measurement of Hazardous Gases, Heinemann, Exeter, 29-67 (1981).

* cited by examiner

POWER REDUCTION IN COMBUSTIBLE GAS SENSORS

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Catalytic or combustible (flammable) gas sensors have been in use for many years to, for example, prevent accidents caused by the explosion of combustible or flammable gases. In general, combustible gas sensors operate by catalytic oxidation of combustible gases.

The operation of a catalytic combustible gas sensor proceeds through electrical detection of the heat of reaction of a combustible gas on the oxidation catalysts, usually through a resistance change. The oxidation catalysts typically operate in a temperature above 100° C. (and, more typically, above 300° C.) to catalyze combustion of an analyte (for example, in the range of 350 to 600° C. temperature range for methane detection). Therefore, the sensor must sufficiently heat the sensing element through resistive heating. In a number of combustible gas sensors, the heating and detecting element are one and the same and composed of a platinum alloy because of its large temperature coefficient of resistance and associated large signal in target/analyte gas. The heating element may be a helical coil of fine wire or a planar meander formed into a hotplate or other similar physical form. The catalyst being heated often is an active metal catalyst dispersed upon a refractory catalyst substrate or support structure. Usually, the active metal is one or more noble metals such as palladium, platinum, rhodium, silver, and the like and the support structure is a refractory metal oxide including, for example, one or more oxides of aluminum, zirconium, titanium, silicon, cerium, tin, lanthanum and the like. The support structure may or may not have high surface area (that is, greater than 75 $m^2/g$). Precursors for the support structure and the catalytic metal may, for example, be adhered to the heating element in one step or separate steps using, for example, thick film or ceramic slurry techniques. A catalytic metal salt precursor may, for example, be heated to decompose it to the desired dispersed active metal, metal alloy, and/or metal oxide.

As illustrated in FIGS. 1A and 1B, a number of conventional combustible gas sensors such as illustrated sensor 10 typically include an element such as a platinum heating element wire or coil 20 encased in a refractory (for example, alumina) bead 30, which is impregnated with a catalyst (for example, palladium or platinum) to form an active or sensing element, which is sometimes referred to as a pelement 40, pellistor, detector or sensing element. A detailed discussion of pelements and catalytic combustible gas sensors which include such pelements is found in Mosely, P. T. and Tofield, B. C., ed., *Solid State Gas Sensors*, Adams Hilger Press, Bristol, England (1987). Combustible gas sensors are also discussed generally in Firth, J. G. et al., *Combustion and Flame* 21, 303 (1973) and in Cullis, C. F., and Firth, J. G., Eds., *Detection and Measurement of Hazardous Gases*, Heinemann, Exeter, 29 (1981).

Bead 30 will react to phenomena other than catalytic oxidation that can change its output (i.e., anything that changes the energy balance on the bead) and thereby create errors in the measurement of combustible gas concentration. Among these phenomena are changes in ambient temperature, humidity, and pressure.

To minimize the impact of secondary effects on sensor output, the rate of oxidation of the combustible gas may, for example, be measured in terms of the variation in resistance of sensing element or pelement 40 relative to a reference resistance embodied in an inactive, compensating element or pelement 50. The two resistances may, for example, be part of a measurement circuit such as a Wheatstone bridge circuit as illustrated in FIG. 1C. The output or the voltage developed across the bridge circuit when a combustible gas is present provides a measure of the concentration of the combustible gas. The characteristics of compensating pelement 50 are typically matched as closely as possible with active or sensing pelement 40. In a number of systems, compensating pelement 50 may, however, either carry no catalyst or carry an inactivated or poisoned catalyst. In general, changes in properties of compensating elements caused by changing ambient conditions are used to adjust or compensate for similar changes in the sensing element.

Active or sensing pelement 40 and compensating pelement 50 can, for example, be deployed within wells 60a and 60b of an explosion-proof housing 70 and can be separated from the surrounding environment by a flashback arrestor, for example, a porous metal frit 80. Porous metal frit 80 allows ambient gases to pass into housing 70 but prevents ignition of flammable gas in the surrounding environment by the hot elements. Such catalytic gas sensors are usually mounted in instruments which, in some cases, must be portable or wireless and, therefore, carry their own power supply. It is, therefore, desirable to minimize the power consumption of a catalytic gas sensor.

Oxidation catalysts formed onto a helical wire heater are typically referred to as pelements, while those formed onto hotplates (whether microelectronic mechanical systems (MEMS) hotplates or conventional, larger hotplates) are sometimes known by the substrate. Oxidative catalysts formed on MEMS heating elements are sometimes referred to herein as MEMS pellistors. As described above, the detecting pelements or catalytically active hotplates can be paired with a similarly sized heater coated with materials with similar thermal conductivity as the active catalyst but without active sites. The inactive pelement or hotplate may be used to compensate for changes in ambient temperature, relative humidity, or background thermal conductivity not associated with a combustible gas and are therefore often referred to as compensators. The matched pair of detecting and compensating elements can be assembled in a Wheatstone bridge configuration for operation and combustible gas detection, which requires that both the detector and compensator operate at the same elevated temperature. The high-temperature operation of the catalytic sensing element requires a significant amount of power consumption. Power consumption is particularly a problem in the case of detecting combustible gases as detection should be performed very often or continuously to ensure a safe environment. Portable instrument and wireless installations rely on battery systems for power.

In a number of currently available combustible gas sensors which include sensing and compensating beads, a single, third bead, sometimes referred to as a trigger or a "sniff bead", is included which requires very little power. The trigger bead is not required to provide a linear response and is not required to be immune to positive excursion temperature/humidity fluctuations. With the restrictions of linearity and immunity to positive temperature and humidity fluctuations eliminated, the size and power restrictions of the "trigger" bead may be reduced in comparison to detector beads.

SUMMARY

In one aspect, a sensor system includes electronic circuitry including a control system and a primary combustible gas sensor. The primary combustible gas sensor includes a first primary element in operative connection with the electronic circuitry. The first primary element includes a first primary support structure, a first primary catalyst supported on the first primary support structure and a first primary heating element in operative connection with the first primary support structure. The first primary combustible gas sensor further includes a second primary element in operative connection with the electronic circuitry. The second primary element includes a second primary support structure, a second primary catalyst supported on the second primary support structure and a second primary heating element in operative connection with the second primary support structure.

The sensor system further includes a trigger combustible gas sensor including a first trigger element of low-thermal-mass which includes a first trigger heating element in operative connection with the electronic circuitry. The trigger combustible gas sensor also includes a second trigger element of low thermal mass including a second trigger heating element. The second trigger element is also in operative connection with the electronic circuitry. The electronic circuitry further has a first trigger mode of operating in which the first trigger element is heated to a temperature at or above a temperature at which the first trigger element causes combustion of the at least one combustible gas analyte and wherein the second trigger element is operated as a trigger compensating element.

The electronic circuitry is further configured to operate the trigger combustible gas sensor to detect a value of a response at or above a threshold value. The primary combustible gas sensor is activated (from a low-power state) upon the threshold value being detected by the trigger combustible gas sensor. As used herein, a low-power state includes a zero-power state.

The electronic circuitry may, for example, have a first primary mode of operating in which the first primary element is heated above a temperature at which the first primary catalyst catalyzes combustion of at least one combustible gas analyte and wherein the second primary element is operated as a primary compensating element.

The second primary element may, for example, be operated at a lower power than the first primary element in the first primary mode. In a number of embodiments, the electronic circuitry has a second primary mode of operating in which the second primary element is heated above a temperature at which the first primary catalyst catalyzes combustion of at least one combustible gas analyte and wherein the first primary element is operated as a primary compensating element. The first primary element may, for example, be operated at a lower power than the second primary element in the second primary mode.

In a number of embodiments, the second trigger element is operated at a lower power than the first trigger element in the first trigger mode. The electronic circuitry may, for example, have a second trigger mode of operating in which the second trigger element is heated above a temperature at which the second trigger element causes combustion of at least one combustible gas analyte and wherein the first trigger element is operated as a trigger compensating element. The first trigger element may, for example, be operated at a lower power than the second trigger element in the second trigger mode.

In a number of embodiments, the first trigger element includes a first trigger catalyst, and the second trigger element includes a second trigger catalyst.

In a number of embodiments, the first trigger element includes a first MEMS element and the second trigger element includes a second MEMS element. In a number of embodiments, the value of the response of the trigger combustible gas sensor is a concentration of the at least one combustible gas analyte which is output via a user interface in operative connection with the control system.

In a number of embodiments, during the first trigger mode, the electronic circuitry is configured to periodically cycle the first trigger element between the temperature at or above which the first trigger element causes combustion of the at least one combustible gas analyte and another temperature at which the first trigger element is substantially inactive to cause combustion of the at least one combustible gas analyte. In a number of embodiments, during the second trigger mode, the electronic circuitry is configured to periodically cycle the second trigger element between the temperature at or above which the second trigger element causes combustion of the at least one combustible gas analyte and another temperature at which the second trigger element is substantially inactive to cause combustion of the at least one combustible gas analyte.

A user may, for example, be notified via a user interface in operative connection with the control system when the value of the response of the trigger combustible gas sensor is at or above the threshold value. In a number of embodiments, each of the first trigger element and the second trigger element independently has a thermal time constant no greater than 8 seconds, no greater than 1 second or no greater than 0.250 seconds.

In another aspect, a sensor system includes electronic circuitry including a control system and a primary combustible gas sensor. The primary combustible gas sensor includes a first primary element in operative connection with the electronic circuitry. The first primary element includes a first primary support structure, a first primary catalyst supported on the first primary support structure and a first primary heating element in operative connection with the first primary support structure. The first primary element further includes a second primary element in operative connection with the electronic circuitry. The second primary element includes a second primary support structure, a second primary catalyst supported on the second primary support structure and a second primary heating element in operative connection with the second primary support structure.

The sensor system further includes a trigger combustible gas sensor including a first MEMS trigger element comprising a first trigger heating element. The first trigger MEMS element is in operative connection with the electronic circuitry. The electronic circuitry is configured to heat the first MEMS trigger element to at temperature at or above a temperature at which the first MEMS trigger element causes combustion of the at least one combustible gas analyte. The electronic circuitry is further configured to operate the trigger combustible gas sensor to detect a value of a response at or above a threshold value. The primary combustible gas sensor is activated (from a low-power state) upon the threshold value being detected by the trigger combustible gas sensor.

As described above, the electronic circuitry may, for example, have a first primary mode of operating in which the first primary element is heated to a temperature at or above a temperature at which the first primary catalyst catalyzes combustion of at least one combustible gas analyte and wherein the second primary element is operated as a primary compensating element.

In a number of embodiments, the trigger combustible gas sensor further includes a second MEMS trigger element including a second trigger heating element. The second MEMS trigger element is in operative connection with the electronic circuitry. The second MEMS trigger element is operated as a compensating element in at least one mode of operation of the sensor system. The electronic circuitry may, for example, be configured to periodically cycle the first trigger element between the temperature at or above which the first trigger element causes combustion of the at least one combustible gas analyte and another temperature at which the first trigger element is substantially inactive to cause combustion of the at least one combustible gas analyte. The electronic circuitry may, for example, be configured to periodically cycle the first trigger element between the temperature at or above which the first trigger element causes combustion of the at least one combustible gas analyte and another temperature at which the first trigger element is substantially inactive to cause combustion of the at least one combustible gas analyte. In a number of embodiments, each of the first MEMS trigger element and the second MEMS trigger element independently has a thermal time constant no greater than 1 second, no greater than 0.500 seconds or no greater than 0.250 seconds.

In a further aspect, a method of sensing at least one combustible sensor system, includes providing a system including a control system and a primary combustible gas sensor. The primary combustible gas sensor includes a first primary element in operative connection with the electronic circuitry. The first primary element includes a first primary support structure, a first primary catalyst supported on the first primary support structure and a first primary heating element in operative connection with the first primary support structure. The first primary combustible gas sensor further includes a second primary element in operative connection with the electronic circuitry. The second primary element includes a second primary support structure, a second primary catalyst supported on the second primary support structure and a second primary heating element in operative connection with the second primary support structure. The system further includes a trigger combustible gas sensor including a first trigger element of low-thermal-mass which includes a first trigger heating element in operative connection with the electronic circuitry. The trigger combustible gas sensor also includes a second trigger element of low thermal mass including a second trigger heating element. The second trigger element is also in operative connection with the electronic circuitry. The electronic circuitry further has a first trigger mode of operating in which the first trigger element is heated to a temperature at or above a temperature at which the first trigger element causes combustion of the at least one combustible gas analyte and wherein the second trigger element is operated as a trigger compensating element.

The method further includes operating the electronic circuitry in a first trigger mode in which the first trigger element is heated to a temperature at or above a temperature at which the first trigger element causes combustion of the at least one combustible gas analyte and wherein the second trigger element is operated as a trigger compensating element and activating the primary combustible gas sensor from a low-power state via the electronic circuitry if the trigger combustible gas sensor detects a value of a response at or above a threshold value.

The method may further include, upon activating the primary combustible gas sensor, operating the electronic circuitry in a first primary mode in which the first primary element is heated above a temperature at which the first primary catalyst catalyzes combustion of at least one combustible gas analyte and wherein the second primary element is operated as a primary compensating element. The sensor system may, for example, further be operated as described above.

In still a further aspect, a method includes providing a sensor system including electronic circuitry including a control system and a primary combustible gas sensor. The primary combustible gas sensor includes a first primary element in operative connection with the electronic circuitry. The first primary element includes a first primary support structure, a first primary catalyst supported on the first primary support structure and a first primary heating element in operative connection with the first primary support structure. The first primary element further includes a second primary element in operative connection with the electronic circuitry. The second primary element includes a second primary support structure, a second primary catalyst supported on the second primary support structure and a second primary heating element in operative connection with the second primary support structure. The sensor system further includes a trigger combustible gas sensor including a first MEMS trigger element comprising a first trigger heating element. The first trigger MEMS element is in operative connection with the electronic circuitry. The electronic circuitry is configured to heat the first MEMS trigger element to at temperature at or above a temperature at which the first MEMS trigger element causes combustion of the at least one combustible gas analyte. The electronic circuitry is further configured to operate the trigger combustible gas sensor to detect a value of a response at or above a threshold value. The primary combustible gas sensor is activated (from a low-power state) upon the threshold value being detected by the trigger combustible gas sensor.

The method further includes operating the electronic circuitry to heat the first MEMS trigger element to at temperature at or above a temperature at which the first MEMS trigger element causes combustion of the at least one combustible gas analyte and activating the primary combustible gas sensor from a low-power state via the electronic circuitry upon the threshold value being detected by the trigger combustible gas sensor.

The method may further include, upon activating the primary combustible gas sensor, operating the electronic circuitry in a first primary mode in which the first primary element is heated to a temperature at or above a temperature at which the first primary catalyst catalyzes combustion of at least one combustible gas analyte and wherein the second primary element is operated as a primary compensating element. The sensor system may further be operated as described above.

The present devices, systems, and methods, along with the attributes and attendant advantages thereof, will best be appreciated and understood in view of the following detailed description taken in conjunction with the accompanying drawings.

DETAILED DESCRIPTION

Figure 1B:
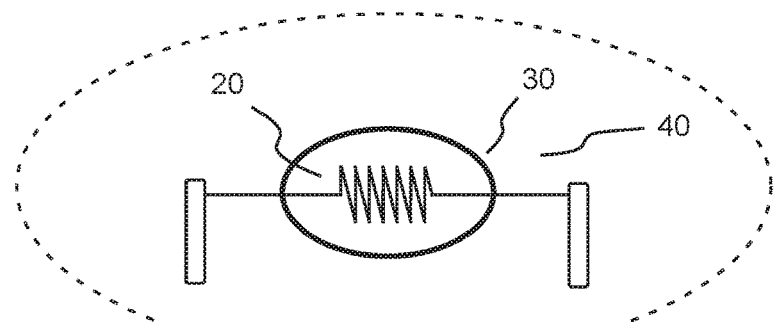
FIG. 1B illustrates schematically an enlarged view of the sensing element of the combustible gas sensor of FIG. 1A.
Figure 1A:
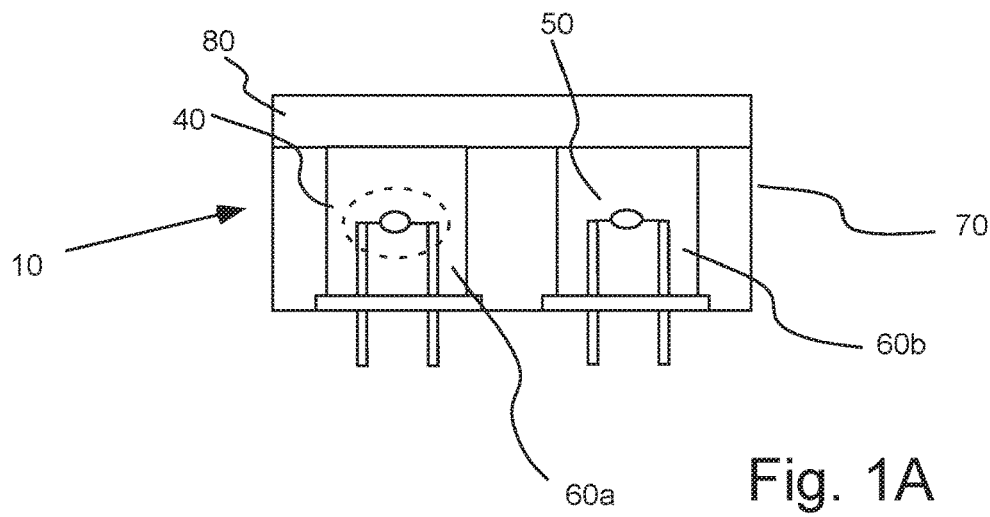
FIG. 1A illustrates schematically an embodiment of a conventional combustible gas sensor.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an element" includes a plurality of such elements and equivalents thereof known to those skilled in the art, and so forth, and reference to "the element" is a reference to one or more such elements and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein include, but is not limited to, hardware, firmware, software or combinations of each to perform a function(s) or an action(s). For example, based on a desired feature or need, a circuit may include a software controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software or combinations of each to perform a function(s) or an action(s), or to cause a function or action from another component. For example, based on a desired application or need, logic may include a software controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "controller," as used herein includes, but is not limited to, any circuit or device that coordinates and controls the operation of one or more input and/or output devices. A controller may, for example, include a device having one or more processors, microprocessors, or central processing units capable of being programmed to perform functions.

The term "logic," as used herein includes, but is not limited to, hardware, firmware, software or combinations thereof to perform a function(s) or an action(s), or to cause a function or action from another element or component. Based on a certain application or need, logic may, for example, include a software controlled microprocess, discrete logic such as an application specific integrated circuit (ASIC), or other programmed logic device. Logic may also be fully embodied as software. As used herein, the term "logic" is considered synonymous with the term "circuit."

The term "software," as used herein includes, but is not limited to, one or more computer readable or executable instructions that cause a computer or other electronic device to perform functions, actions, or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

In a number of embodiment hereof, "trigger" or "sniffer" sensors hereof reduce power requirement and/or provide improved functionality as compared to currently available combustible gas sensors. In a number of embodiments hereof, a sensor having one or more low-thermal-mass elements (for example, a sensing element and a compensating element) such as a Micro-Electro-Mechanical Systems or MEMS or micro-hotplate sensor is used to function as a trigger or sniffer sensor. A MEMS hotplate sensor or other low-thermal-mass trigger sensor hereof may, for example, provide a gas concentration reading. Alternatively the trigger sensor may be used to simply measure a threshold value which triggers activation of a primary, combustible gas sensor, which may be a conventional combustible gas sensor including pelements as described above or may include low-thermal-mass elements as described herein.

When the primary sensor is not activated, the primary sensor may be held in a lower power (for example, a zero power) or OFF state. The primary sensor may, for example, be unable to sense a combustible gas analyte in the OFF state. Upon activation of the primary sensor, the primary sensor is placed in a higher power state or ON state to sense the combustible gas analyte and provide a more accurate reading of gas concentration. Whether the trigger sensor is used only to determine that a threshold response value has been reached or the measured threshold response value provides a measure of concentration of a combustible gas analyte, the measure of the threshold response value may cause an notification or alert to be issued to the user.

In general, operation of the trigger or sniffer sensor to activate a primary sensor as described herein, reduces power requirements as compared to operation of the primary sensor without the trigger or sniffer sensor. In a number of embodiments in which the trigger sensor provides or outputs a concentration of a combustible gas analyte, the primary sensor is configured to provide or output a more accurate concentration reading and/or a concentration reading over a broader range of concentrations. Typically, but not necessarily, the element or elements of the trigger sensor hereof are of a lower thermal mass than the elements of the primary sensor. The trigger sensor may be continue to be activated or may be deactivated when the primary sensor is activated.

MEMS elements have not previously been used in the function of a trigger sensor. As further described below, low-thermal-mass, low-thermal-time-constant elements hereof may also be operated in a non-continuous or pulsed manner to further decrease power consumption as compared to continuously powered trigger sensors. Moreover, in a number of embodiments, a trigger sensor hereof may include both a sensing element and a compensating element, which may, for example, provide for a compensated reading of a combustible analyte gas concentration from the trigger sensor. A user may, for example, be notified or alerted of a concentration measure by the trigger sensor and/or if a measured value of a trigger sensor response (which may, for example, be relatable to a concentration) exceeds a threshold value.

Low thermal time constants associated with low thermal mass sensors assist in providing quick response times, reducing the time an element may be unavailable for use in a detection mode and decrease power requirements. In a number of embodiments, trigger or sniffer sensors hereof (and/or low-thermal-mass primary sensors hereof) have an element having a thermal time constant of 8 second or less, 6 seconds or less, 1 second or less, 0.5 seconds or less or 0.250 second or less. A low thermal mass/low thermal time constant sensor may, for example, include a MEMS pellistor as described above or a pelement of low thermal mass to provide a thermal time constant. As used herein the thermal time constant of an element is defined as the time required to change 63.2% of the total difference between its initial and final temperature when subjected to a step function change in drive power, under zero power initial conditions. MEMS pellistors typically have a lower thermal time constant than low-thermal-mass pelements. MEMS pellistors may, for example, have thermal time constants of 1 second or less, 0.5 seconds or less or 0.250 second or less.

In general MEMS elements for sensors hereof have a dimension less than 1 mm. Such element may be manufactured via a microfabrication technique. In a number of representative embodiments, sensing elements may be manufactured with a thick film layer suitable to cause combustion of an analyte gas upon heating to a predetermined temperature. Sensor elements hereof may be powered to an operating temperature by resistive heating and to detect combustible gases analytes. In a number of representative embodiments, the thickness and diameter for a MEMS hotplate oxidative film is 15 microns and 650 microns, respectively.

In a number of embodiments, beads or pelements of low thermal mass and having low thermal constants as described above may be used as trigger sensor elements as well as primary sensor element hereof. Low-thermal-mass/low-thermal-time constant pelements are, for example, discussed in U.S. Pat. No. 8,826,721, the disclosure of which is incorporated herein by reference. Such pelements may, for example, have a diameter less than 500 μm or have a volume less than a sphere having a diameter 500 μm. In general, trigger sensors hereof need only sufficient thermal mass to generate a measurable signal in the presence of an analyte gas.

Oxidative layers of trigger elements hereof may, but need not, include a catalyst. In the case that a catalyst is used the oxidative layer may cause combustion of a combustible gas analyte at a lower temperature (for example, in the range of 100 to 700° C.) than in the absence of a catalyst. For example, a temperature above 700° C. or above 900° C. may be required to induce oxidation/combustion of the combustible gas analyte in connection with an element not including a catalyst.

Conventional catalytic combustible gas sensor elements and/or low-thermal-mass sensor elements hereof may be operated in a Wheatstone bridge as, for example, described in connection with FIG. 1B. Primary or trigger sensors hereof may, for example, be operated in constant current, constant voltage, or constant resistance. As described above, catalytic elements of a combustible gas sensor are operated in, for example, a temperature range of 100 to 700° C. whenever the sensor is operational. A mode of operation of a sensor at constant current or at constant voltage may be termed a "continuous" mode of operation.

An alternate operational mode, which is particularly suitable for low-thermal-mass pelements such as MEMS hotplates/pellistors, is to quickly heat and cool a sensor elements or elements in a pulsed power mode. An advantage to operating in pulse mode is significantly lower power consumption as compared to continuous mode. Another advantage is improved span response as a result of adsorption of excess combustible gas on the catalyst at cooler temperatures during unpowered or lower powered operation (that is, during a REST time) as compared to continuously powering the catalyst at the run temperature of 100 to 700° C.

Pulse width modulation may, for example, be used to control the energy delivered to the heating element(s) of the trigger and primary sensors hereof. Pulse width modulation is a well-known control technique used to control the average power and/or energy delivered to a load. In embodiments hereof, a voltage is supplied to, for example, a MEMS hotplate or other heating element to heat the oxidative layer and supported catalyst/structure, when present, to a desired temperature. Because the trigger sensors hereof have relatively low thermal mass, the cycle times can be relatively short.

In a pulse mode of operation, heating energy (that is, heating voltage(s) or heating currents(s)) may be periodically supplied to the heating element(s) during an "ON time" in a "pulse mode". Rest energy (that is, rest voltage(s) or a rest current(s)), which is less than the heating energy may be supplied during a "REST time". The total of the higher-energy or ON time plus the lower-energy or REST time correspond to a cycle time or a cycle duration. Gas concentration of the analyte is measured during the ON time. The heating energy (voltages/currents) supplied during the ON time may be constant during the ON time or may be varied (for example, supplied as heating voltage/current plateau or as heating voltage/current ramp). The rest energy (voltages/currents) may be equal to zero, or be sufficiently lower than the heating energy so that the trigger gas sensor does not interact in a significant manner with (or consume any or substantially any) gas to be detected. Similar to the ON time, the rest energy supplied during the REST time may be constant during all of the REST time or may be varied (for example, supplied as rest voltage/current plateau or as rest voltage/current ramp). The cycle may be repeated.

The ON time duration may, for example, be in the range of 100 msec to 1 second or in the range of 300 msec to 500 msec in a number of embodiments hereof. In a number of embodiments, the ON time duration may be kept as short as possible to improve response time. In a number of embodiments, the duty cycle may, for example, be in the range of 5% to 12% (ratio of ON time/(ON time+REST time). In a number of embodiments, the ON time is approximately 350 msec (that is, equal to or within 10% of that) and the duty cycle is approximately 10% (that is, equal to or within 20% of that value). In a representative example, the cycle time or cycle duration was 4000 msec, during which the ON time was 350 msec and the REST time was 3650 msec. Therefore, the duty cycle is 8.75%.

Figure 2A:
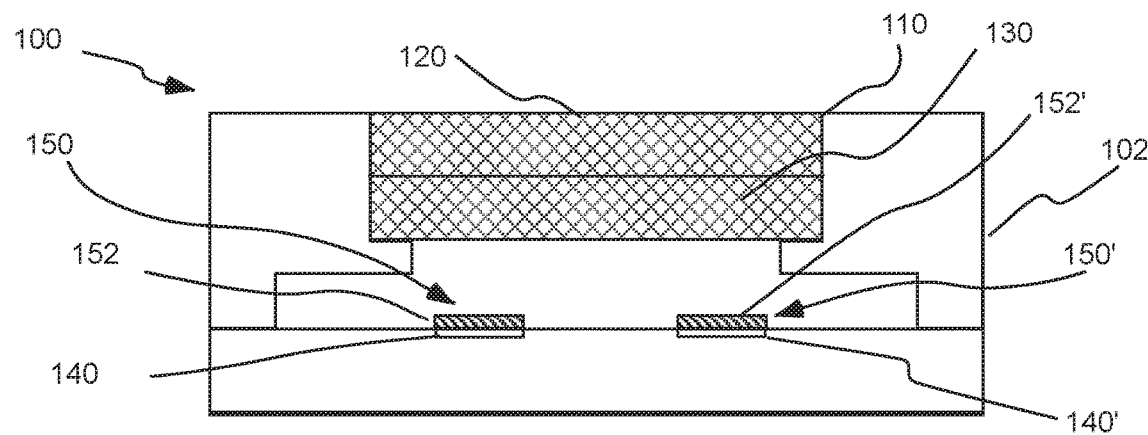
FIG. 2A illustrates schematically a cross-sectional view of an embodiment of a low-thermal mass combustible gas sensor suitable for use herein.
Figure 2B:
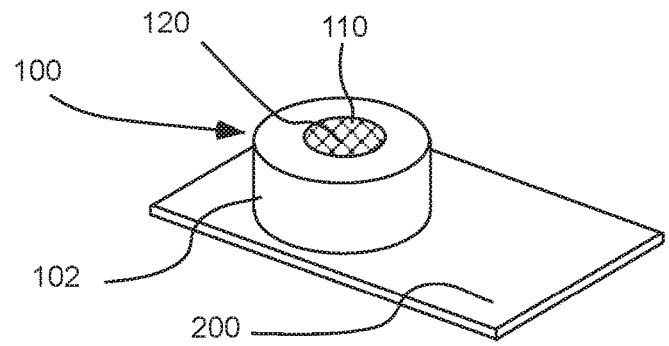
FIG. 2B illustrates a perspective view of the low-thermal-mass combustible gas sensor of FIG. 2A in operative connection with a printed circuit board.

FIG. 2A illustrates a cutaway view of an embodiment of a MEMS or micro-hotplate trigger sensor hereof, which includes a housing 102 having a gas inlet 110. A screen or cap 120, which may include or function as a filter 130, may, for example, be placed in connection with inlet 110. The energy (current and voltage) used in MEMS micro-hotplate trigger sensor 100 may, for example, be sufficiently low to provide intrinsic safety such that a flashback arrestor, as known in the combustible gas detector arts, may not be necessary. As described above, flashback arrestors (for example, porous frits) allow ambient gases to pass into a housing but prevent ignition of combustible/flammable gas in the surrounding environment by hot elements within the housing. One or more heating elements or hotplates 140 may, for example, be used to heat an oxidative layer 152 (which may, for example, be an oxidative catalyst layer) of a first MEMS element or pellistor 150 to a first operating temperature. In a number of embodiments, a second MEMS element or second pellistor 150' may be included within MEMS hotplate trigger sensor 100 to be heated to a second operating temperature.

In a number of embodiments, first MEMS element 150 may be operated as a sensing or detecting element and second MEMS element 150' may be operated as a compensating element as known in the combustible gas sensor arts. In other embodiments, as further described below, the operation of MEMS elements 150 and 150' may be switched by altering the mode of operation thereof.

In a number of embodiments, the operation of a particular element as a sensing element or a compensating element may be controlled by controlling the operating temperature thereof. If the operating temperature of an element is maintained at or above a temperature at which gas will combust at the surface thereof, it may be operated as a sensing element. If the operating temperature of an element is maintained below a temperature at which gas will combust at the surface thereof, it may be operated as a compensating element. The temperature at which gas will combust at the surface of an element depends upon the composition of that surface. Surfaces including a catalytic material will typically cause combustion at a temperature (a catalytic light-off temperature) lower than a surface not including a catalytic material.

If operated solely as a MEMS compensator element 150' may, for example, include an inactive layer 152' which may be heated by one or more heating elements or hotplates 140'. In this case, the second operating temperature may be maintained at a temperature lower than the temperature required to cause combustion at a surface thereof in the absence of a catalyst. Alternatively layer 152' may include an active catalyst and be operated at a sufficiently low temperature to prevent catalytic oxidation of combustible gas at the surface thereof.

Figure 1C:
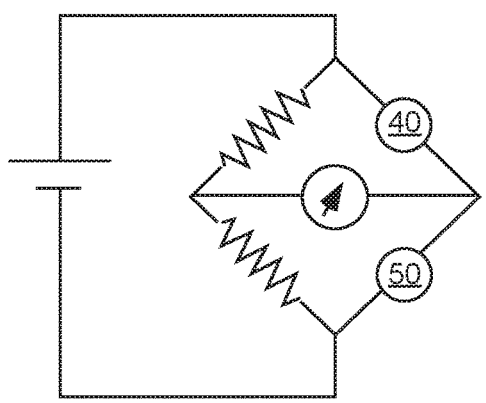
FIG. 1C illustrates a schematic view of a Wheatstone bridge circuit incorporating the sensing element and the compensating element of the combustible gas sensor of FIG. 1A.

MEMS hotplate sensor 100 may, for example, mounted on a printed circuit board or PCB 200. The two resistances of the sensing element 150 and the compensating element may, for example, be part of a measurement circuit such as a Wheatstone bridge circuit as illustrated in FIG. 1C or a simulated Wheatstone bridge circuit. A representative example of a MEMS hotplate sensor suitable for use herein is a SGX MP7217 hotplate sensor or pellistor available from SGX Sensortech, SA of Corcelles-Coromondreche, Switzerland. Such a MEMS hotplate sensor is disclosed, for example, in U.S. Pat. No. 9,228,967, the disclosure of which is incorporated herein by reference.

Figure 2C:
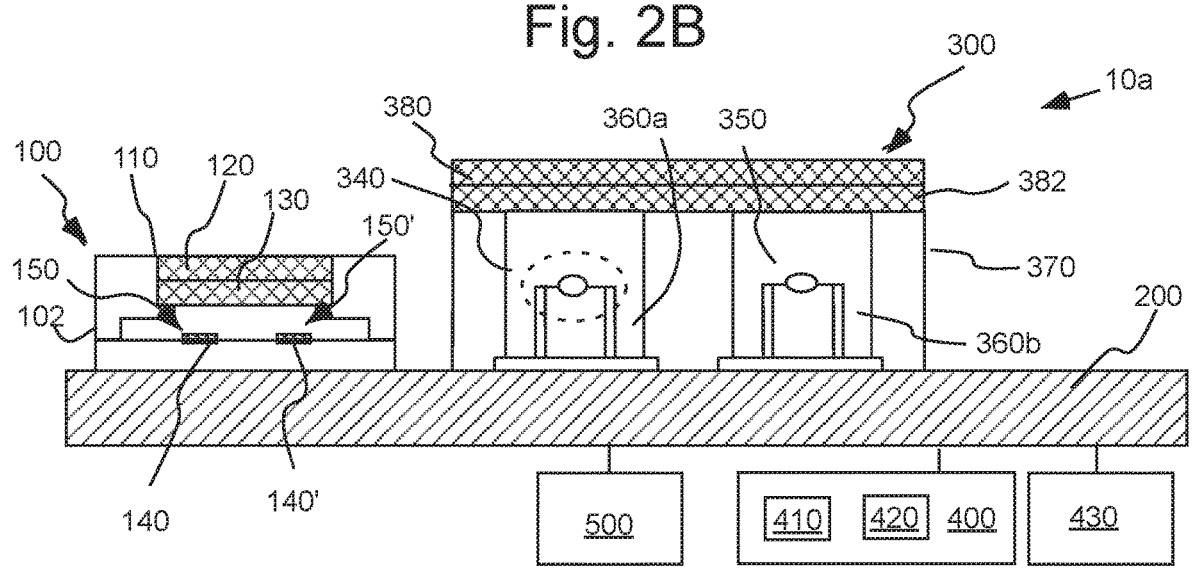
FIG. 2C illustrates schematically a cross-sectional view of a system hereof including a conventional combustible gas sensor and a combustible gas sensor including a sensing element and a compensating element of low thermal mass.

The devices and systems hereof may, for example, be deployed either as a two-sensor system or the low-thermal-mass trigger sensor can be embedded into a single combustible gas sensor that, for example, includes a primary combustible gas sensor, which provides a calibrated response which is dependent upon analyte gas concentration. The primary combustible gas sensor may, for example, be a traditional or conventional catalytic bead system, a lower-thermal-mass pelement system or a low-thermal-mass MEMS system. FIG. 2C schematically illustrates an embodiment of a sensor system or device 10a hereof which includes a MEMS hotplate combustible gas sensor 100 as a trigger combustible gas sensor and a conventional combustible gas sensor 300 as a primary combustible gas sensor. As illustrated in FIG. 2C, MEMS hotplate combustible gas sensor 100 and combustible gas sensor 300 may, for example, be placed in operative connection with a control system 400 and a power source 500 (for example, a battery system including one or more batteries) via PCB 200.

The electronic circuitry of sensor system or device 10a may, for example, be in operative connection with each of MEMS micro-hotplate, trigger combustible gas sensor 100 and primary combustible gas sensor 300 to, for example, control power to the sensors (as described above) and to process an output signal from the sensors. The electronic circuitry of sensor system 10 may, for example, include or be in operative connection with a control system or controller including a processor system 410 (including, for example, one or more processors such as microprocessors) and a memory system 420. One or more algorithms for control of sensor 100 and sensor 300 and/or for processing of data may, for example, be stored in memory system 420, which is in operative connection with processor system 430. Output of sensors 100 and/or 300 may, for example, be provided to a user or users via a user interface 430 (for example, including one or more devices for input/output of information including a touch screen display, a speaker etc.) in operative connection with processor system 410. A user interface 430 may, for example, be provided as a component of the combustible gas sensor system or device 10*a* and/or remote from the combustible gas sensor. An alarm signal may, for example, be generated via the electronic circuitry and provided to a user via one or more components of user interface 430 (for example, visually, audibly etc.).

As described above, for combustible gas sensor system of device 10, primary combustible gas sensor 300 includes a first element or pelement 340 and second element or pelement 350. As described above, one of the first element 340 and second element 350 is operated as a sensing element, while the other of first element 340 and second element 350 is operated as a compensating element. Once again, the function of an element can, for example, be controlled by the mode of operation/operating temperature thereof. The temperature may be controlled by control of the power provided to the element. The two resistances may, for example, be part of a measurement circuit such as a Wheatstone bridge circuit as illustrated in FIG. 1C. The characteristics of second pelement 350 may be matched as closely as possible with active or sensing pelement 340. In a number of embodiments in which second element 350 is operated solely as a compensating pelement, second element 350 may, for example, either carry no catalyst or carry an inactivated or poisoned catalyst.

In the illustrated embodiment, first element or pelement 340 and second element or pelement 350 are positioned within wells 360*a* and 360*b* of an explosion-proof housing 370 and can be separated from the surrounding environment by a flashback arrestor, for example, a porous metal frit 380. A filter element 382 may also be present.

In operation of system or device 10*a* in a first mode, MEMS hotplate trigger sensor 100 is operated to detect a change in the analyte gas or gases entering system or device 10*a*, while primary combustible gas sensor 300 is maintained in a low power, inactive, or OFF state. If a response signal from MEMS hotplate trigger sensor 100 is determined by control system 200 to indicate that the concentration of one or more analyte gases has changed or has changed in an amount above a predetermined threshold, a second mode of operation is initiated and activation of primary combustible gas sensor 300 occurs (that is, a powered, active or ON state of primary combustible gas sensor 300 is activated).

As described above, trigger sensors hereof need not be, but may be "diagnostic" sensors with sufficient characteristics to provide an accurate indication of the concentration of the combustible gas analyte being sensed. Such characteristics would include, for example, sufficient response range to provide accurate indications of gas content over a desired range of concentration, long-term baseline stability, significant resistance to changes arising from environmental conditions, etc. The trigger sensors hereof may be "non-diagnostic" or "pseudo-diagnostic." In that regard, the trigger sensors may have sufficient range and accuracy to be useful to accomplish the trigger function described herein. Stability and accuracy are not as important in this functionality inasmuch as non-conservative false negative deviations are avoided. In a number of embodiments, there is no need to refer to an earlier established calibration event in the case of non-diagnostic trigger sensor hereof. In the case of a non-diagnostic trigger sensor, a compensating element may not be required.

Providing both a first MEMS or other low-thermal-mass element and a second MEMS or other low-thermal-mass element in a trigger sensor hereof requires very little energy for operation. Unlike previous attempts to provide a trigger sensor or monitor in which only nondiagnostic or nonspecific changes in gas concentration are detected by a single trigger bead, the combustible gas, trigger sensors hereof may provide a relatively accurate output of gas concentration. In that regard, the MEMS or other low-thermal-mass combustible gas trigger sensors hereof provide a compensated gas concentration output or reading that may be posted to a user while the primary combustible sensor (for example, a pelement-based sensor 300) is inactive and/or when activated and warming up sufficiently to take a reading. Moreover, a reading or measurement from the a micro-hotplate or other low-thermal-mass trigger sensor hereof may be used to activate an alarm level if needed.

Even in the case in which a trigger sensor hereof include only a single element, use of a MEMS element provides significant reductions in power requirements as compared to currently available trigger beads. Moreover, whether a trigger sensor hereof include one or two elements, significant reductions in power requirements may be achieved by operation in a pulsed mode.

As described above, providing a low-power trigger sensor can reduce required power by allowing very low power (including zero power) operation of a primary, higher-power, analytical sensor until the secondary, trigger sensor detects a change or a threshold change in concentration of a combustible gas. Operating a trigger sensor in a pulse mode, as described herein, provides an intermediate monitoring of the gas mixture of the environment in fluid connection with the sensor device, system or instrument.

As also described above, the first primary element 340 and second primary element 350 may be operated in a cyclic mode as, for example, disclosed in U.S. Pat. Nos. 8,826,721 and 9,625,406. In that regard, a sensor may be cycled between a first mode in which first primary element 340 is operated in a higher power mode and second primary element 350 is operated in a lower power mode and a second mode in which second or compensating element is operated in a higher power mode and the first or sensing element is operated in a lower power mode. In that regard, the electronic circuitry of the system hereof may, for example, be adapted to or configured to cycle between a first mode in which the first primary element is operated in a higher power (high temperature) mode and the second sensing element is operated in a lower power (lower temperature) mode and a second mode in which the second sensing element is operated in a higher power (higher temperature) mode and the first sensing element is operated in a lower power (lower temperature) mode. In the first mode, the second sensing element can, for example, be used to compensate for ambient temperature changes. In the second mode, the first sensing element can, for example, be used to compensate for ambient temperature changes. The electronic circuitry can, for example, be adapted to periodically switch between the first mode and the second mode. The electronic circuitry can, for example, be adapted to switch between the first mode and the second mode upon a manually controlled event. The manually controlled event can, for example, include a power on event.

Similarly, first trigger element 140 and second trigger element may be operated in a cyclic mode as disclosed in U.S. Pat. Nos. 8,826,721 and 9,625,406. In that regard, one may cycle between a first mode in which first trigger element 150 is operated in a higher power mode and second trigger element 150' is operated in a lower power mode and a second mode in which second trigger element 150' is operated in a higher power mode and first trigger element 150 is operated in a lower power mode.

Testing has, for example, been conducted wherein elements were operated at relatively low currents (for example, as low as 1/20 of the normal operating current) to monitor the effect of changes in ambient temperature only. In such an operating mode, the elements require, for example, only a few milliwatts or less to operate. The results of such testing indicate that elements operated at low power (that is, sufficiently low power to reduce the catalytic or other activity of the element, for example, to render the element substantially or completely inactive with respect to combustible gas), can be used as a replacement for a traditional compensating element. Since pressure effects are negligible and only wire chemistry temperature effects are significant in the element, the need to match such sensing/compensating elements precisely is significantly relaxed.

Elements of sensors hereof may be switched between a high power/high temperature active mode and a low power/low temperature inactive or compensating mode over a wide range of periods. In general, the period of cycling is limited (on the lower end) by the amount of time required to achieve equilibrium or steady state operation (that is, by the thermal time constants of the element). Electronic circuitry hereof, can, for example, effect automatic periodic switching between sensing element modes.

Other power/temperature control modes for combustible gas sensor elements which may, for example, be used to limit catalyst inhibition are disclosed in U.S. patent application Ser. Nos. 15/597,933 and 15/597,859, the disclosures of which are incorporated herein by reference. Such methodologies may be readily adapted for use herein.

U.S. Pat. Nos. 8,826,721, 4,533,520 and 5,780,715 disclose systems and methods to, for example, balance bridges electronically and to operate sensing elements independently. Such systems and methods can, for example, be incorporated in circuitry hereof.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A sensor system, comprising:
electronic circuitry comprising a control system;
a primary combustible gas sensor comprising a first primary element in operative connection with the electronic circuitry and comprising a first primary support structure, a first primary catalyst supported on the first primary support structure and a first primary heating element in operative connection with the first primary support structure; a second primary element in operative connection with the electronic circuitry and comprising a second primary support structure, a second primary catalyst supported on the second primary support structure and a second primary heating element in operative connection with the second primary support structure; and
a trigger combustible gas sensor comprising a first trigger element of low-thermal-mass comprising a first trigger heating element, the first trigger element being in operative connection with the electronic circuitry, and a second trigger element of low thermal mass comprising a second trigger heating element, the second trigger element being in operative connection with the electronic circuitry, the electronic circuitry having a first trigger mode of operating in which the first trigger element is heated to a temperature at or above a temperature at which the first trigger element causes combustion of at least one combustible gas analyte and wherein the second trigger element is operated as a trigger compensating element, wherein during the first trigger mode the electronic circuitry is configured to periodically cycle the first trigger element between the temperature at or above which the first trigger element causes combustion of the at least one combustible gas analyte and another temperature at which the first trigger element is substantially inactive to cause combustion of the at least one combustible gas analyte;
the electronic circuitry being configured to activate the primary combustible gas sensor from a low-power state upon a threshold value being detected by the trigger combustible gas sensor.

2. The sensor system of claim 1 wherein the electronic circuitry has a first primary mode of operating during activation thereof in which the first primary element is heated above a temperature at which the first primary catalyst catalyzes combustion of the at least one combustible gas analyte and wherein the second primary element is operated as a primary compensating element.

3. The sensor system of claim 2 wherein the second primary element is operated at a lower power than the first primary element in the first primary mode.

4. The sensor system of claim 3 wherein the electronic circuitry has a second primary mode of operating in which the second primary element is heated above a temperature at which the second primary catalyst catalyzes combustion of at least one combustible gas analyte and wherein the first primary element is operated as a primary compensating element.

5. The sensor system of claim 4 wherein the first primary element is operated at a lower power than the second primary element in the second primary mode.

6. The sensor system of claim 1 wherein the second trigger element is operated at a lower power than the first trigger element in the first trigger mode.

7. The sensor system of claim 6 wherein the electronic circuitry has a second trigger mode of operating in which the second trigger element is heated above a temperature at which the second trigger element causes combustion of the at least one combustible gas analyte and wherein the first trigger element is operated as a trigger compensating element.

8. The sensor system of claim 7 wherein during the second trigger mode the electronic circuitry periodically cycles the second trigger element between the temperature at or above which the second trigger element causes combustion of the at least one combustible gas analyte and another temperature at which the second trigger element is substantially inactive to cause combustion of the at least one combustible gas analyte.

9. The sensor system of claim 7 wherein the first trigger element is operated at a lower power than the second trigger element in the second trigger mode.

10. The sensor system of claim 9 wherein the first trigger element comprises a first trigger catalyst and the second trigger element comprises a second trigger catalyst.

11. The sensor system of claim 1 wherein the first trigger element comprises a first trigger catalyst and the second trigger element comprises a second trigger catalyst.

12. The sensor system of claim 1 wherein the first trigger element comprises a first MEMS element and the second trigger element comprises a second MEMS element.

13. The sensor system of claim 1 wherein the value of the response of the trigger combustible gas sensor is a concentration of the at least one combustible gas analyte which is output via a user interface in operative connection with the control system.

14. The sensor system of claim 1 wherein the electronic circuitry comprises a processor system and a memory system, the memory system comprising one or more algorithms stored therein to control operation of the sensor system.

15. The sensor system of claim 1 wherein a user is notified via a user interface in operative connection with the control system when the value of the response of the trigger combustible gas sensor is at or above the threshold value.

16. The sensor system of claim 1 wherein each of the first trigger element and the second trigger element independently has a thermal time constant no greater than 8 seconds.

17. The sensor system of claim 1 wherein each of the first trigger element and the second trigger element independently has a thermal time constant no greater than 1 second.

18. The sensor system of claim 1 wherein each of the first trigger element and the second trigger element independently has a thermal time constant no greater than 0.250 seconds.

19. A sensor system, comprising:
electronic circuitry comprising a control system;
a primary combustible gas sensor comprising a first primary element in operative connection with the electronic circuitry and comprising a first primary support structure, a first primary catalyst supported on the first primary support structure and a first primary heating element in operative connection with the first primary support structure; a second primary element in operative connection with the electronic circuitry and comprising a second primary support structure, a second primary catalyst supported on the second primary support structure and a second primary heating element in operative connection with the second primary support structure; and
a trigger combustible gas sensor comprising a first MEMS trigger element comprising a first trigger heating element, the first trigger MEMS element being in operative connection with the electronic circuitry, the electronic circuitry being configured to heat the first MEMS trigger element to at or above a temperature at which the first MEMS trigger element causes combustion of at least one combustible gas analyte wherein the electronic circuitry is configured to periodically cycle the first trigger element between the temperature at or above which the first trigger element causes combustion of the at least one combustible gas analyte and another temperature at which the first trigger element is substantially inactive to cause combustion of the at least one combustible gas analyte;
the electronic circuitry further being configured to activate the primary combustible gas sensor from a low-power state upon the threshold value being detected by the trigger combustible gas sensor.

20. The sensor system of claim 19 wherein the electronic circuitry has a first primary mode of operating in which the first primary element is heated to a temperature at or above a temperature at which the first primary catalyst catalyzes combustion of the at least one combustible gas analyte and wherein the second primary element is operated as a primary compensating element.

21. The sensor system of claim 19 wherein the trigger combustible gas sensor further comprises a second MEMS trigger element comprising a second trigger heating element, the second MEMS trigger element being in operative connection with the electronic circuitry, wherein the second MEMS trigger element is operated as a compensating element in at least one mode of operation of the sensor system.

22. The sensor system of claim 19 wherein the electronic circuitry comprises a processor system and a memory system, the memory system comprising one or more algorithms stored therein to control operation of the sensor system.

23. The sensor system of claim 21 wherein the electronic circuitry periodically cycles the first trigger element between the temperature at or above which the first trigger element causes combustion of the at least one combustible gas analyte and another temperature at which the first trigger element is substantially inactive to cause combustion of the at least one combustible gas analyte.

24. The sensor system of claim 21 wherein each of the first MEMS trigger element and the second MEMS trigger element independently has a thermal time constant no greater than 1 second.

25. The sensor system of claim 21 wherein each of the first MEMS trigger element and the second MEMS trigger element independently has a thermal time constant no greater than 0.500 seconds.

26. The sensor system of claim 21 wherein each of the first MEMS trigger element and the second MEMS trigger element independently has a thermal time constant no greater than 0.250 seconds.

* * * * *

UNITED STATES PATENT AND TRADEMARK OFFICE
CERTIFICATE OF CORRECTION

PATENT NO. : 10,900,922 B2  
APPLICATION NO. : 16/037882  
DATED : January 26, 2021  
INVENTOR(S) : Michael Alvin Brown, Meghan E. Swanson and Mark Flori Zanella, Sr.

Page 1 of 1

It is certified that error appears in the above-identified patent and that said Letters Patent is hereby corrected as shown below:

In the Specification  
Column 9, Line 39 delete "continue" and insert --continued--.  
Column 12, Line 64 delete "system 10" and insert --system 10a--.  
Column 13, Line 6 delete "processor system 430" and insert --processor system 410--.  
Column 13, Line 19 delete "device 10" and insert --device 10a--.  
Column 14, Line 29 delete "include" and insert --includes--.  
Column 15, Line 4 delete "first trigger element 140" and insert --first trigger element 150--.

In the Claims  
Column 18, Claim 19, Line 6 after "analyte" insert a --,--.

Signed and Sealed this  
Sixth Day of April, 2021

Drew Hirshfeld  
*Performing the Functions and Duties of the*  
*Under Secretary of Commerce for Intellectual Property and*  
*Director of the United States Patent and Trademark Office*